(12) United States Patent
Hadoux et al.

(10) Patent No.: US 12,408,833 B2
(45) Date of Patent: Sep. 9, 2025

(54) NON-MYDRIATIC HYPERSPECTRAL OCULAR FUNDUS CAMERA

(71) Applicant: CENTRE FOR EYE RESEARCH AUSTRALIA LIMITED, East Melbourne (AU)

(72) Inventors: Xavier Hadoux, East Melbourne (AU); Maxime Jannaud, East Melbourne (AU); Francis Labrecque, East Melbourne (AU); Peter Van Wijngaarden, East Melbourne (AU)

(73) Assignee: CENTRE FOR EYE RESEARCH AUSTRALIA LIMITED, East Melbourne (AU)

( * ) Notice: Subject to any disclaimer, the term of this patent is extended or adjusted under 35 U.S.C. 154(b) by 423 days.

(21) Appl. No.: 18/005,415

(22) PCT Filed: Jul. 14, 2021

(86) PCT No.: PCT/AU2021/050754
§ 371 (c)(1),
(2) Date: Jan. 13, 2023

(87) PCT Pub. No.: WO2022/011420
PCT Pub. Date: Jan. 20, 2022

(65) Prior Publication Data
US 2023/0255470 A1 Aug. 17, 2023

(30) Foreign Application Priority Data
Jul. 14, 2020 (AU) ................. 2020902430

(51) Int. Cl.
*A61B 3/00* (2006.01)
*A61B 3/10* (2006.01)

(52) U.S. Cl.
CPC .......... *A61B 3/0008* (2013.01); *A61B 3/0025* (2013.01); *A61B 3/10* (2013.01)

(58) Field of Classification Search
CPC ....... A61B 3/0008; A61B 3/0025; A61B 3/10; A61B 3/12; A61B 5/0075; A61B 5/0079;
(Continued)

(56) References Cited

U.S. PATENT DOCUMENTS 8,109,635 B2   2/2012   Allon et al.
8,491,120 B2   7/2013   Kahn
(Continued)

FOREIGN PATENT DOCUMENTS

WO   WO 2011/029064 A1   3/2011
WO   WO 2015/003274 A1   1/2015
WO   WO 2020/047594 A1   3/2020
WO   WO 2022/011420 A1   1/2022

OTHER PUBLICATIONS

EP 21841266.6 Extended European Search Report mailed Jun. 17, 2024.
(Continued)

*Primary Examiner* — Jack Dinh
(74) *Attorney, Agent, or Firm* — ALSTON & BIRD LLP

(57) ABSTRACT

Described herein is an ocular fundus imaging apparatus (11) including and an illumination module (140) and an imaging module (141). The illumination module (140) includes light sources (103, 104) configured to generate light at wavelengths within a desired spectral range. A first optical assembly is provided to shape and direct the light onto an eye (102) of a subject. A tuneable bandpass filter (109) selects a wavelength sub-interval within the desired spectral range. The imaging module (141) includes a second optical assembly to collect light returned from the eye (102) of the subject and to project the returned light from the eye (102) onto an image sensor (113). The second optical assembly
(Continued)

includes one or more optical elements capable of compensating for ocular variation. The image sensor (113) is configured to image the returned light to generate an image of the ocular fundus at the wavelength sub-interval.

20 Claims, 13 Drawing Sheets

(58) Field of Classification Search
CPC ............... A61B 5/4058; A61B 5/6821; A61B 2560/0223; H04N 23/74; H04N 23/75; H04N 23/959

See application file for complete search history.

(56) References Cited

U.S. PATENT DOCUMENTS

| | | |
|---|---|---|
| 8,807,751 B2 | 8/2014 | Kahn |
| 2007/0002276 A1 | 1/2007 | Hirohara et al. |
| 2010/0026957 A1 | 2/2010 | Tanguay, Jr. et al. |
| 2012/0169995 A1 | 7/2012 | Mohr et al. |
| 2013/0296709 A1 | 11/2013 | Zuzak et al. |
| 2018/0064334 A1 | 3/2018 | Izawa |
| 2018/0209850 A1 | 7/2018 | Raz et al. |

OTHER PUBLICATIONS

International Search Report and Written Opinion for PCT/AU2021/050754, mailed Sep. 27, 2021.

Dwight, et al., "Lenslet Array Tunable Snapshot Imaging Spectrometer (LATIS) for Hyperspectral Fluorescence Microscopy," Biomedical Optics Express 1950, vol. 8, No. 3 (Mar. 1, 2017).

NON-MYDRIATIC HYPERSPECTRAL OCULAR FUNDUS CAMERA

CROSS-REFERENCE TO RELATED APPLICATIONS

This application is a national phase entry of International Application No. PCT/AU2021/050754, filed Jul. 14, 2021, which claims priority to Australian Application No. 2020902430, filed Jul. 14, 2020, the contents each of which are hereby incorporated by reference in their entirety.

TECHNICAL FIELD

The present disclosure relates to the field of optical fundus imaging. Embodiments of the disclosure relate to an ocular fundus imaging apparatus, a method to compensate for non-homogeneity of images recorded by an ocular fundus imaging apparatus and a method to recover spectral information of a sample from a plurality of independent spectral measurements.

Some embodiments of the present disclosure provide a system and method to record a non-mydriatic hyperspectral image of the ocular fundus of a subject. However, it will be appreciated that the disclosure has other applications including multispectral imaging and mydriatic imaging.

BACKGROUND

The importance of colour: Ocular fundus cameras are low powered microscopes that can image the fundus of the eye at high resolution. Conventional fundus cameras use a bright flash of broad spectrum 'white' light to illuminate the fundus via an arrangement of optical elements that direct and shape the light as well as an imaging system that receives the light reflected from the eye. The imaging sensor of a conventional colour fundus camera is designed to resolve the structure (spatial detail) of the retina using combinations of three colour channels (red, green and blue). These colour channels are tuned to simulate the sensitivities of the three visual pigments in the human cone photoreceptors. As a result, an image captured by such a camera consists of combinations of these colour channels and closely resembles what is directly observed by the human eye on clinical examination of the retina with an ophthalmoscope or slit lamp and hand-held fundus lens.

The spectral properties of a light source have an influence on the sensitivity of a given fundus camera for particular spatial features, including anatomical structures and disease features. For example, the use of a blue shifted light source or a blue-green filter can be used to provide a "red-free" image to highlight retinal blood vessels and haemorrhages. This demonstrates that altering the spectral composition of the illuminating light in fundus imaging can provide clinically useful information that is not available via conventional colour fundus photography.

A hyperspectral ocular fundus camera shares many features in common with a conventional fundus camera, but it has the added capability of recording the intensity of reflected light from the eye at many (typically greater than 20) discrete wavelengths of light (spectral sub-intervals). Accordingly, hyperspectral fundus cameras have both high spatial and spectral resolution. A multispectral fundus camera also acquires images at different wavelengths of light but these are fewer in number, of non-equal spectral width and may be overlapping.

Multispectral and hyperspectral camera definitions: Multispectral and hyperspectral fundus cameras acquire spatially- and spectrally-resolved images, enabling the detection of biomarkers that cannot be detected with conventional colour fundus cameras. Hyperspectral usually refers to imaging systems that acquire a series of images using narrow, non-overlapping or minimally overlapping and equally sampled wavebands of light within a main wavelength range. The term multispectral imaging is usually reserved for imaging systems that acquire a series of images using a smaller number (typically between 3 to 15) of wavebands within a main wavelength range. These multispectral wavebands are often overlapping and of non-equal bandwidths. In the context of hyperspectral and/or multispectral ocular fundus imaging, the main wavelength range typically spans the visible light spectrum and near infrared wavelengths, or parts thereof.

While both hyperspectral and multispectral cameras provide more spectral information than is provided by conventional colour fundus cameras, the main advantage of hyperspectral cameras is that as the imaging wavebands are narrow, each waveband is independent of the next and therefore better suited for both visualization and analytics. However, hyperspectral cameras are more complicated to engineer than multispectral cameras.

Multispectral/hyperspectral fundus cameras: Multiple solutions for multispectral and hyperspectral imaging have been proposed. Pixel scanning is a method that records a single spectral pixel and moves the sampling in both spatial dimensions. An alternative to scanning in two dimensions is using a push broom acquisition. In push broom imaging, a narrow strip of the fundus is imaged and the spectral component of the reflected light is dispersed on the sensor in a direction that is perpendicular to the scanning axis. Whilst this approach is widely used in remote sensing, as the movement of a satellite serves as the scanning direction, it is more difficult to apply to fundus imaging due to rapid movements (saccades) of the eye, which require complex post-processing alignments.

Snapshot fundus hyperspectral cameras record spectral and spatial dimensions in a single frame, using either extended Bayer patterns on the sensor or optical techniques to split the different spectral bands to different parts of the camera sensor. This technique can give high acquisition rates, but at the expense of spectral and spatial resolution. Currently the only suitable solution for multispectral or hyperspectral imaging without compromising spatial resolution is to scan along the spectral dimension. However, during the period of this scanning process, fast movements of the eye can affect the measurements.

The challenge of light power: For patient acceptability, fundus imaging needs to be performed within seconds. This interval decreases to 300 milliseconds or less for non-mydriatic (without the aid of pharmacologic pupil dilation) imaging, as this corresponds with the latency of the pupillary light reflex, whereafter pupil constriction impairs image quality. As the efficiency of fundus cameras is very low (a minority of the light from the illumination source reaches the fundus of the eye and only a small fraction of this is reflected from the fundus to the camera sensor) achieving high quality images at multiple wavebands within a short time frame is technically challenging.

Any discussion of the background art throughout the specification should in no way be considered as an admission that such art is widely known or forms part of common general knowledge in the field.

SUMMARY

Noting the above limitations, the inventors have identified a need for an improved apparatus and method to acquire non-mydriatic hyperspectral images of the fundus of the eye.

In particular, the inventors have identified that trying to achieve good chromatic aberration compensation with a conventional colour camera is complex since all the photons of different wavelengths arrive on the sensor at the same time. This can typically only be corrected for using expensive lens systems that aim at correcting those aberrations to an extent. However, if the objective lens of the camera becomes complex, it becomes increasingly difficult to compensate for some of the internal back reflections in the camera (stray light).

In the following, there is described an apparatus that uses the full resolution of a camera sensor to acquire images of the fundus with high spectral and spatial resolutions. The spectral band can be continuously tuned within the spectral range of interest (for example 420 to 760 nm) using a linearly variable bandpass filter.

Furthermore, there is described a method to synchronise the movement of this linearly variable bandpass filter with the illumination power and image acquisition to achieve a high SNR through the whole spectral range of interest. The apparatus described herein is fast enough for high quality non-mydriatic fundus image acquisition (image capture within 300 milliseconds). In a further embodiment, a spectral information recovery method/system is described whereby images acquired using at least partially overlapping wavebands of variable spectral width are processed to derive an accurate representation of a hyperspectral profile as if they were acquired with narrow, independent and equally sampled wavebands. In a further embodiment, there is disclosed a method/system to reduce chromatic aberrations of the recorded images. Some embodiments of this disclosure can be achieved with low-cost components, including a broadband diffused light source (LED) and variable bandpass filter.

One embodiment of the present disclosure provides an apparatus capable of providing a spectrally- and spatially-resolved image of the fundus of the eye of a subject in non-mydriatic conditions. The apparatus includes an optical lens assembly (termed illumination path) which projects the light from a spectrally tuneable light source onto the fundus of a subject. This assembly is also used to shape the light into an annulus on the pupil plane of the subject to minimise reflection from the cornea. The tuneable light source is configured to produce light with various spectral profiles. The spectral profile does not need to be monochromatic or limited to the minimal bandwidth necessary to resolve the spectral features of interest, nor have a high out-of-band rejection, as these parameters are compensated for following acquisition using the spectral information recovery method disclosed herein. The apparatus also includes an imaging optical assembly to project the light reflected from the fundus of a subject onto a camera sensor. The said camera is synchronized with the illumination power and variable bandpass filter position to enhance the signal-to-noise ratio (SNR). The apparatus further contains a gaze alignment system to help the subject to fixate. The gaze alignment system can be switched off during image capture so that it does not contribute to the recorded image.

In a further embodiment there is provided a spectral information recovery method/system whereby images acquired using at least partially overlapping wavebands of potentially variable spectral width are processed to derive an accurate representation of a hyperspectral profile acquired with narrow, independent and equally sampled wavebands.

In accordance with a first aspect of the present invention, there is provided an ocular fundus imaging apparatus including:
an illumination module having:
one or more light sources configured to generate light at wavelengths within a desired spectral range;
a first optical assembly to shape and direct the light onto an eye of a subject; and
a tuneable bandpass filter to select a wavelength sub-interval within the desired spectral range; and
an imaging module having:
a second optical assembly to collect light returned from the eye of the subject and to project the returned light from the eye onto an image sensor, the second optical assembly including one or more optical elements capable of compensating for ocular variation; and
an image sensor configured to image the returned light to generate an image of the ocular fundus at the wavelength sub-interval;
wherein the tuneable bandpass filter and the image sensor are synchronized so as to capture images at different wavelength sub-intervals within the desired spectral range.

In some embodiments, the tuneable bandpass filter is tuneable between the infrared wavelength range and the blue wavelength range. In some embodiments, the tuneable bandpass filter is configured to be tuned from the infrared wavelength range to the blue wavelength range such that the image sensor captures one or more first images in the infrared wavelength range and subsequently captures one or more second images in the visible wavelength range.

In some embodiments, the tuneable bandpass filter is configured to be tuned with predefined steps at a predefined speed.

In some embodiments, the power of the one or more light sources is controlled to provide a respective predefined power level for each of the spectral sub-intervals.

In some embodiments, the respective predefined power levels for each of the spectral sub-intervals are selected to compensate for spectral non-flatness arising from one or more of the illumination module and/or imaging module.

In some embodiments, the power of the one or more light sources is controlled to achieve a threshold signal-to-noise ratio for the tissue being imaged.

In some embodiments, the power of the one or more light sources is controlled to obtain a target digital count value on the image sensor for a reference surface. In some embodiments, the reference surface is derived from a retinal reflectivity of a sample population.

In some embodiments, the power of the one or more light sources is controlled to compensate for an optical absorption by the illumination and/or imaging modules.

In some embodiments, the power of the one or more light sources is controlled based on a sensitivity of the imaging sensor.

In some embodiments, the second optical assembly includes a focusing lens sub-system having one or more focusing lenses moveable in position along an optical axis, and wherein the axial movement of the one or more focusing lenses is synchronized with a wavelength filter movement of the tuneable bandpass filter to give an improved focusing at the image sensor for each of a plurality of spectral sub-intervals to compensate for chromatic aberrations.

In some embodiments, the focusing lens movement is nonlinear with respect to the wavelength tuning of the tuneable bandpass filter. In some embodiments, the focusing lens movement is quadratic with respect to the wavelength tuning of the tuneable bandpass filters.

In some embodiments, the one or more light sources is an LED having a spectral bandwidth covering at least the range from 450 nm to 720 nm.

In some embodiments, the tuneable bandpass filter has a spectral bandwidth that is larger than the steps between the wavelength sub-intervals.

In some embodiments, the tuneable bandpass filter is a linearly variable bandpass filter.

In some embodiments, the illumination module includes an annulus disposed after the tuneable bandpass filter for shaping the light at a pupil plane of the eye of the subject.

In some embodiments, the apparatus includes an optical diffuser disposed between the tuneable bandpass filter and annulus.

In some embodiments, the apparatus includes a homogenizing rod disposed between the tuneable bandpass filter and annulus. In some embodiments, the optical diffuser is integral with or attached to the homogenizing rod.

In some embodiments, the illumination module includes a black dot optical mask configured to reduce light reflected back to the image sensor.

In some embodiments, the one or more light sources include a first LED having output power in the infrared wavelength range and a second LED having output power in the visible range.

In some embodiments, the apparatus includes a holed mirror disposed at a junction of the illumination and imaging modules, the holed mirror including an outer reflective region for reflecting light from the illumination module to the eye and a central aperture for passing light returned from the eye to the imaging module.

The apparatus of any one the preceding claims wherein the image is captured under non-mydriatic imaging conditions.

In accordance with a second aspect of the present invention, there is provided a method to compensate for non-homogeneity of images recorded by an ocular fundus imaging apparatus, the fundus imaging apparatus including a tuneable bandpass filter to select a wavelength sub-interval within a desired spectral range and a focusing lens moveable in position along an optical axis of the apparatus, the method including the steps:
　recording a baseline image at a predetermined wavelength sub-interval and at a predetermined focusing lens position to image internal reflections from components within the apparatus, wherein the baseline image is an image taken by the apparatus in the absence of an eye and external light at an objective imaging position;
　capturing an image of the fundus of an eye by the apparatus at the predetermined wavelength sub-interval and at the predetermined focusing lens position to generate an original image of the fundus; and
　subtracting the baseline image from the original image to generate a first corrected image to compensate for internal reflections of the apparatus.

In some embodiments, the method includes the step of recording baseline images for a plurality of wavelength sub-intervals and focusing lens positions.

In some embodiments, the method includes the steps of:
　placing an eye model at the objective imaging position of the apparatus, the eye model including a retinal surface of known reflectivity;
　recording an image of the eye model at the predetermined wavelength sub-interval and at the predetermined focusing lens position to generate a reference image;
　subtracting the first corrected image from the reference image to generate a compensated image to compensate for intensity inhomogeneity of the apparatus; and
　dividing the first corrected image by the compensated image to obtain a second corrected image.

In some embodiments, the method includes performing the step of recording an image of the eye model for a plurality of wavelength sub-intervals and focusing lens positions to generate a plurality of reference images.

In accordance with a third aspect of the present invention, there is provided a method of recovering spectral information of a sample from a plurality (K) of independent spectral measurements taken under K spectral illumination profiles, wherein at least two of the spectral illumination profiles are at least partially overlapping, the method including the steps:
　determining spectral filter profiles for each of the K spectral illumination profiles;
　populating a filter matrix of the K filter profiles;
　inverting the filter matrix to generate an inverse filter matrix; and
　multiplying the K spectral measurements by the inverted filter matrix to calculate spectral information of the sample.

In some embodiments, the K spectral illumination profiles are generated from a light source spectral profile passed through a filter tuned across K filter positions.

In some embodiments, the K spectral illumination profiles are within a spectral band of 450 nm to 750 nm.

In some embodiments, the method includes the steps of:
　populating a calibration matrix with information from one or more of an image sensor sensitivity, light source illumination spectrum and optical system spectral transfer function; and
　multiplying the K spectral measurements by the calibration matrix.

In some embodiments, the spectral illumination profiles are measured or estimated on $P>=K$ wavebands. In some embodiments, the K spectral measurements with the calibration matrix yields a P dimensional vector that needs down sampling. In some embodiments, the down sampling is performed with a uniform gaussian down sampling matrix.

In accordance with a fourth aspect of the present invention, there is provided a method of recovering spectral information of a sample from a hyperspectral or multispectral image including a plurality (K) of images of the sample, each image captured under illumination from one or more light sources at a different wavelength sub-interval of a desired spectral range by moving a tuneable filter between K filter positions and recording corresponding images at a digital image sensor, the method including:
　determining a spectral response of the image sensor at each of the K filter positions;
　determining a filter transmission spectrum at each of the K filter positions;
　determining a spectral profile of the light source at each of the K filter positions;
　determining a calibration matrix representing a combination of the image sensor spectral responses, filter transmission spectra and light source spectral profiles;

multiplying the K images of the sample by the inverse of the calibration matrix to calculate spectral information of the sample.

BRIEF DESCRIPTION OF THE DRAWINGS

Example embodiments of the disclosure will now be described, by way of example only, with reference to the accompanying drawings in which.

DETAILED DESCRIPTION

System Overview

Figure 1:
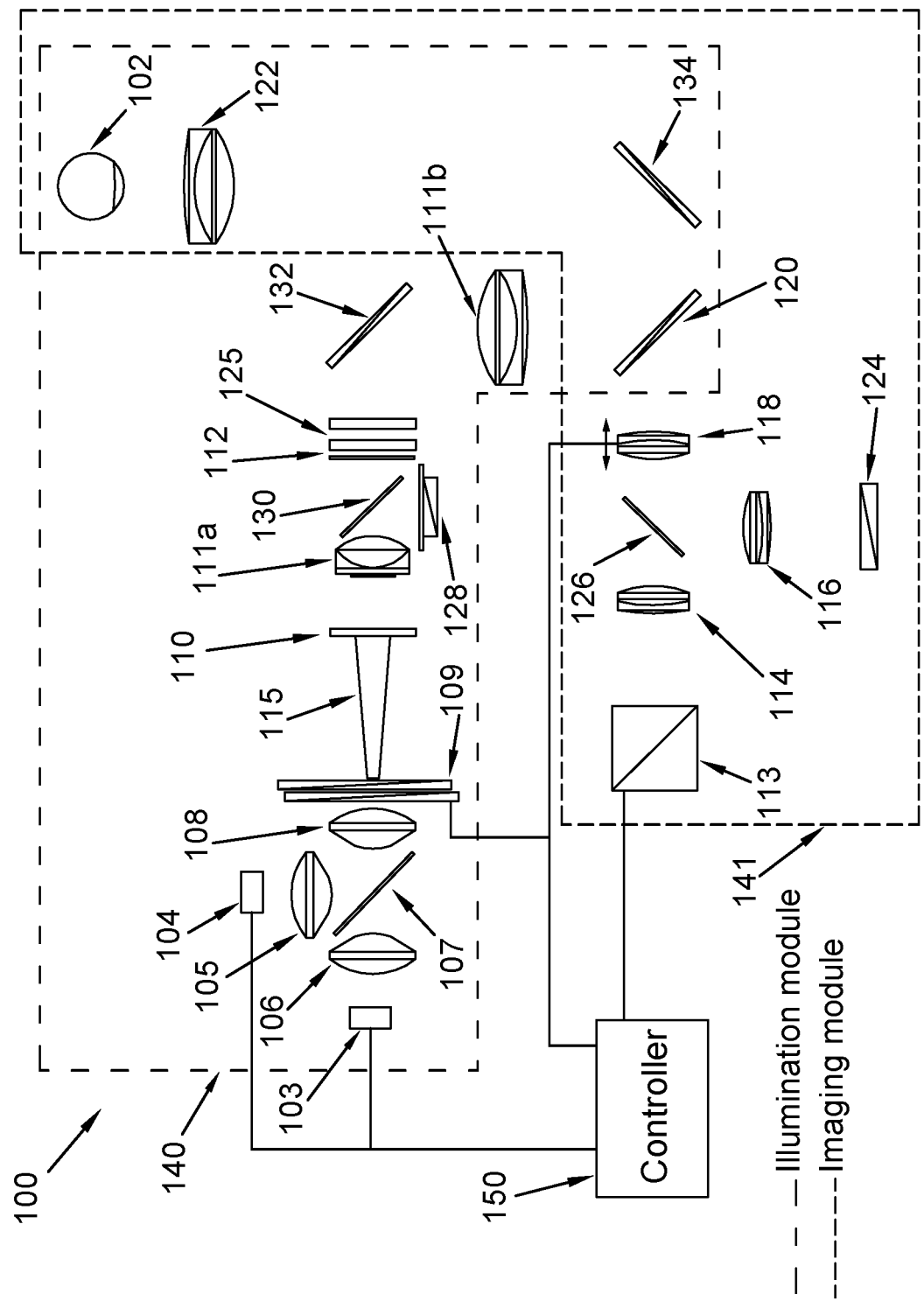
FIG. 1 is a schematic illustration of a retinal imaging apparatus for imaging an ocular fundus of a subject.

Referring initially to FIG. 1, there is illustrated an ocular fundus imaging apparatus 100 for imaging a fundus of an eye 102 of a subject. Ocular fundus imaging systems such as apparatus 100 are configured for the detection and monitoring of various diseases of the eye and body, including disorders of the central nervous system and circulatory system. Fundus cameras are low powered microscopes designed to illuminate and simultaneously image the light reflected from the fundus of a subject. Apparatus 100 can generally be divided into an illumination module 140, indicated by the larger dashed line in FIG. 1, and an imaging module 141, indicated by the smaller dashed line in FIG. 1.

Light is generated by one or more light sources 103 and 104, such as LEDs, which project light having a desired spectral range into a forward illumination path. Preferably, the desired spectral range covers at least the range from 450 nm to 720 nm and optionally some infrared wavelengths (e.g. 850 nm) for camera/eye alignment. The power generated by light sources 103 and 104 is controlled such that the total power incident onto eye 102 is within safe levels according to ISO/ANSI standards. Preferably, one light source is configured to illuminate in the infrared range and one light source is configured to illuminate across a broadband spectrum of the visible range as white light. Illumination in the infrared range can be used to perform initial alignment of the instrument to a subject and illumination across the visible range can be used for standard imaging of the fundus. Although two light sources are illustrated in FIG. 1, it will be appreciated that a single light source or more than two light sources may be incorporated into apparatus 100 to span different spectral ranges of interest.

The light from light sources 103 and 104 is at least partially collimated by respective collimating lenses 105 and 106 and combined together using a beam splitter 107. Collimating lenses 105 and 106 are positioned relative to respective light sources 103 and 104 to optimise the collimation. The collimating lenses should have a high numerical aperture and be positioned at a distance close to their focal length from light sources 103 and 104. In the illustrated embodiment, light sources 103 and 104 are disposed perpendicular to each other and beam splitter 107 is oriented at 45 degrees to the optical axes of both light sources 103 and 104. In this configuration, a portion of light from light source 103 is directed through beam splitter 107 and a portion is combined with a portion of light from light source 104 reflected off beam splitter 107. By way of example, beam splitter may be a 50/50 beam splitter configured to reflect 50% of the incoming light and reflect the remaining 50% of the incoming light. However, it will be appreciated that other configurations of beam splitter and/or other optical elements may be implemented to combine light from more than one light source. In some embodiments, beam splitter 107 may include a glass plate or a removable mirror (actioned by an actuator linked to the controller).

At the output of beam splitter 107, the light from both sources 103 and 104 is spatially combined and co-propagates in a collimated or partially collimated manner. A focussing lens 108 focusses the combined collimated beams onto a tuneable bandpass filter in the form of linearly variable bandpass filter 109. At this point, it is preferable for the spot size of the combined collimated beams to be as small as possible so that most of the partially collimated beam is able to pass through lens 108. As such, focussing lens 108 is preferably a high numerical aperture lens. Filter 109 is preferably positioned at a distance from focussing lens 108 that is close to its focal length. To help with optical aberrations, preferably focussing lens 108 has the same or similar characteristics and dimensions to that of collimating lenses 105 and 106. The passband of filter 109 is selectively controlled by a controller 150 to filter the incoming light to produce a filtered light beam. The operation of filter 109 is described below. In other embodiments, other types of tuneable bandpass filter may be used in place of linearly variable bandpass filter 109.

After passing through filter 109, the light tends not to be spectrally homogeneous in one or more spatial dimensions. For example, if filter 109 is set to have a passband centred at 525 nm with a bandwidth of 50 nm, the left part of the light will contain more power at 500 nm and the right part more power at 550 nm. The filtered light beam in the illumination path is passed through a homogenizing rod and diffuser 115, which forms the filtered light beam into a well-defined output beam of predetermined size having more evenly distributed energy across the beam. The light passing through the homogenizing rod is internally reflected and exits the rod re-homogenised. The diffuser is disposed at the end of the rod and help with this homogenizing process. At the end of diffuser 115, the filtered light beam is not collimated but diffuse in nature.

The homogenized filtered light beam is then shaped by an annulus 110 disposed at or near the end of diffuser 115 to produce an annulus of light. The size of annulus 110 depends on the optics in the illumination path, but its inner/outer diameter is proportional to the desired annulus shape to be formed at a pupil plane for imaging the eye 102.

After being passed through annulus 110, the homogenized and filtered annulus of light is passed through a series of lenses (e.g. relay lenses 111a and 111b) and at least one field stop 112, so that it creates an annulus of light of a predefined size at a pupil plan of the eye 102 and so that the light on fundus of a subject is relatively homogeneous over the desired field of view. Field stop 112 includes a circular aperture of a predetermined diameter such that the light of a suitable field of view is incident onto eye 102. A black dot 125 may be inserted after field stop 112 to perform a masking effect. The black dot is an optical mask element that includes a central dark spot surrounded by a transparent region. The black dot is located at an optical conjugate position to an objective lens 122 described below and reduces the light reflected back onto an image sensor 113 from a centre of the objective lens 122. The helps to avoid saturation of the image sensor 113. The size of black dot 125 needs to be large enough to remove the unwanted reflection but not too large to not mask too much of the light that need to go on the fundus of eye 102.

Preferably, only light from the fundus of eye 102 is imaged by image sensor 113. Any other light from cornea, iris, lens, or internal to the system is considered stray light. Other internal black dots and light baffles may be added to remove additional stray light in the system.

The annulus 110 is imaged on the reflective face of a holed mirror 120 described below and projected towards the objective lens 122.

In the imaging path (the return path of light), the light reflected from the subject's fundus is projected onto an imaging sensor 113 using a series of lenses (e.g. lenses 114 and 118) and an aperture stop defined at least in part by a holed mirror 120.

Figures 2A, 2B:
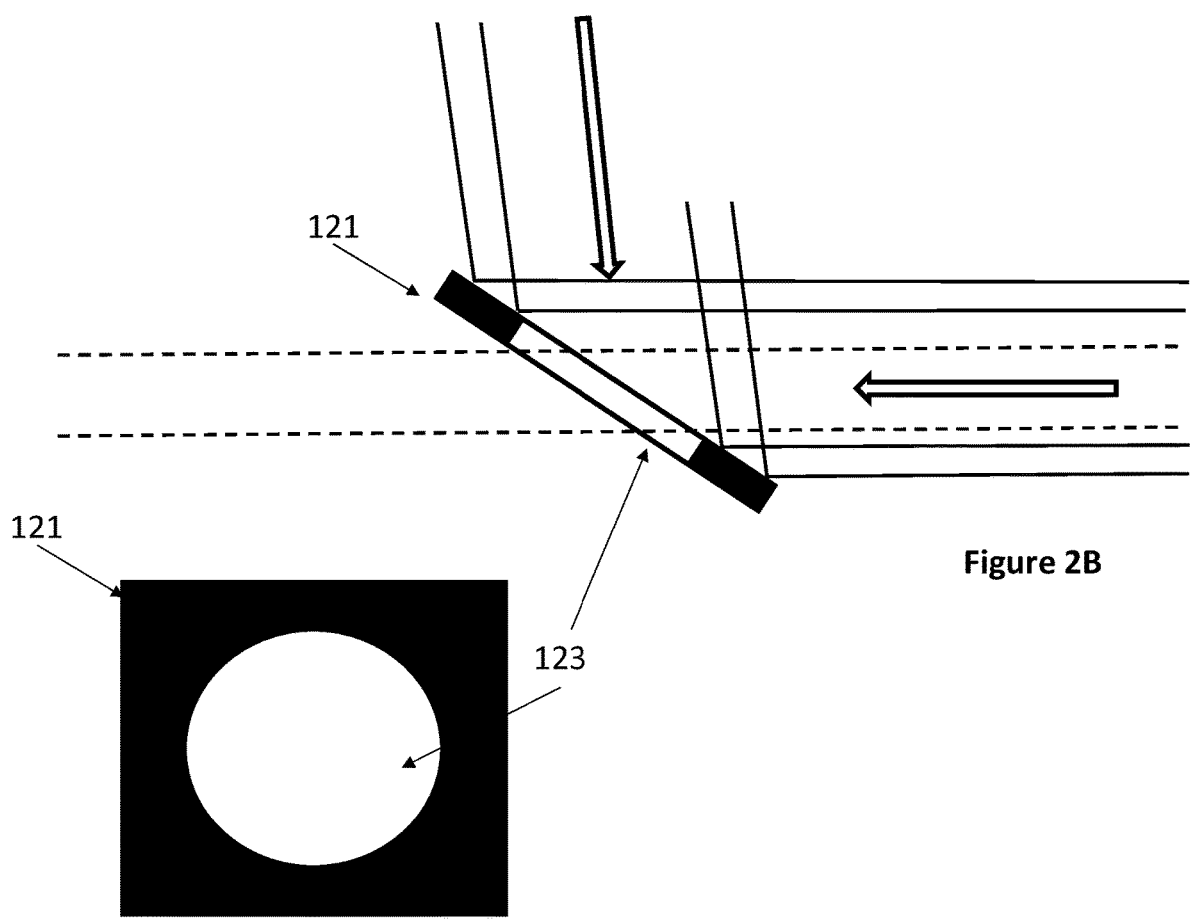
FIG. 2A is a front view of a holed mirror.
FIG. 2B is a side view of holed mirror illustrated reflecting an incoming illumination beam and transmitting a returned light beam.

Referring to FIG. 2A, holed mirror 120 includes a planar mirror 121 having a centrally disposed aperture 123. Holed mirror 120 is positioned along the optical path such that, in the forward illumination direction, the annulus of light is reflected off the outer section of mirror towards eye 102. This is illustrated by the solid lines in FIG. 2B. In the return imaging direction, light reflected off fundus of eye 102 is passed through the central aperture of holed mirror 120, as illustrated by the dashed lines in FIG. 2B. In this manner, holed mirror 120 facilitates the coupling of the forward illumination path and return imaging path. As illustrated in FIG. 1, holed mirror 120 is preferably tilted to direct the incoming and returned light along different trajectories. In other embodiments, this coupling may be achieved with a beam splitter used in place of holed mirror 120.

Light from the illumination path is reflected by the surface of mirror 120 towards the eye and the light exiting the eye 102 in the imaging path passes through the hole in the mirror 120. An objective lens 122, placed between the mirror 120 and the eye 102, is used by both the illumination and the imaging path. In the imaging path, an aerial image of the fundus is formed after the objective lens 122.

An aperture stop situated behind or within the holed mirror 120 limits the amount of light directed toward the sensor 113. The aperture stop is ideally placed conjugate to the pupil of the eye 102 so that it only admits rays that are exiting the fundus from within the illumination annulus. The aerial image is re-imaged on the sensor 113 with a series of lenses, 114 and 118.

As can be seen in FIG. 1, holed mirror 120, objective lens 122 and eye 102 are common to both the illumination module 140 and imaging module 141.

Imaging sensor 113 is used to capture images of the eye 102 at times that are synchronised with passband wavelengths of filter 109 being centred at predefined wavelengths. This corresponds to predefined filter positions of tuneable filter elements as described below. In some embodiments, a single controller 150 is used to control both the filter passband of filter 109 and sensor integration time or shutter period of image sensor 113 in a synchronous manner. However, it will be appreciated that more than one controller may be implemented within apparatus 100. Controller 150 and/or other controllers may be implemented as digital processors, integrated circuits, microcontrollers, system on chip or other conventional hardware having appropriate hardware drivers installed as hardware and/or software, and associated memory for storing data.

Defocus due to the effects of axial length variation and refractive error of the eye may be adjusted with a focus/zoom lens 118 that refocuses the light to provide a sharp image on the sensor 113. Lens 118 is mounted to be linearly axially moved by an actuator that is configured to adjust the position of lens 118 along the optical axis. Focusing lenses 114 and 116 may also be moved in conjunction with movement of lens 118. Control of the movement of lenses 114, 116 and 118 may be performed by respective control signals from controller 150.

A gaze alignment/fixation target 124 such as an LED or LCD screen is placed conjugate to the subject fundus and is used to facilitate gaze alignment and thus the eye position when the subject views target 124. For gaze alignment, the subject is asked to look through objective lens 122 and stare at target 124. Illumination using infrared light can be used for alignment so as not to distract the subject. The position/orientation of apparatus 100 is then controlled in three dimensions to be aligned with eye 102. The axial position of focussing lens 118 is then adjusted so that the eye is in focus for subsequent imaging. The alignment process can be repeated each time a different region of eye 102 is to be imaged. A beam splitter 126, flip mirror or transparent piece of glass or plastic can be used to integrate the gaze alignment system with the rest of the apparatus. The gaze alignment/fixation target is preferably activated during an initial alignment and calibration routine and subsequently switched off during normal image acquisition to avoid unwanted reflection on image sensor 113.

A power meter 128 (or spectrometer/spectroradiometer) may be used to measure the light for verification or calibration purposes during acquisition. A beam splitter 130 disposed between relay lens 111 and field stop 112 can be used to tap off a portion of the collimated and filtered annulus of light to integrate the power-meter 128 with the rest of the apparatus 100. Folding mirror/s 132 and 134 can be used to reduce the spatial footprint of apparatus 100 when integrated into an apparatus. One or more additional folding mirrors may be implemented to vary the spatial shape of the overall apparatus, as illustrated in an alternative embodiment shown in FIG. 11. Power meter 128 may be positioned anywhere in the illumination path after filter 109, but the closer it is to field stop 112, the more likely the light is spatially homogeneous and comparable to the light arriving on the fundus.

As mentioned above, one or multiple light sources can be used in combination to span different spectral ranges of interest. For non-mydriatic imaging, the gaze alignment and focusing is performed with the tuneable filter 109 set to let pass infrared light or moved out of the optical path in order to avoid pupil constriction. Preferably, one light source is configured to illuminate in the infrared range for alignment and another light source illuminates broadband white light across the visible range for actual imaging of eye 102.

Apparatus 100 is capable of non-mydriatic hyperspectral ocular fundus imaging using a combination of one or more high-power LEDs 103 and 104, a linearly variable bandpass filter 109 and light mixing components to homogenise the light. For example, since the light coming from each side of the tuneable bandpass filter 109 will exit the filter with a spectral gradient, a system to mix the light is necessary to ensure homogeneous illumination of the fundus.

In one embodiment of the apparatus 100, an aperture of 2 mm or larger may be used with apparatus 100, thereby permitting a greater amount of light for imaging eye 102. In other embodiments, an aperture smaller than 2 mm is used to provide narrower wavebands with the side effect of having less power compared to the 2 mm or greater aperture. It is possible to achieve the required illumination power density with spectral band as narrow as 50 nm. Accordingly, there is sufficient power for high-quality non-mydriatic imaging with acquisition times at or below 300 milliseconds.

Wavelength Selection

Figure 3:
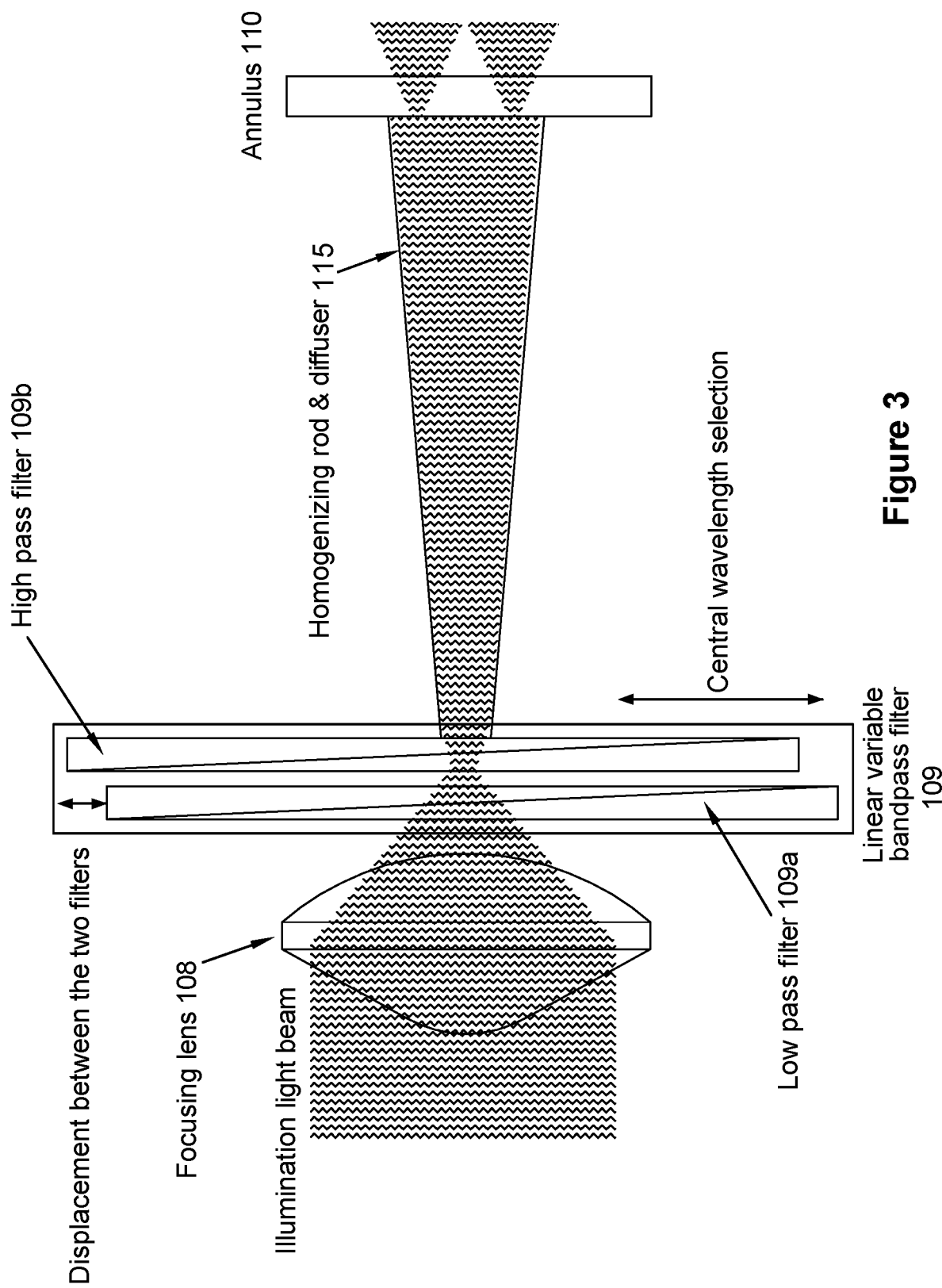
FIG. 3 is a close-up schematic view of linearly variable filter, diffuser and homogenising rod.

Referring now to FIG. 3, there is illustrated a close up of apparatus 100 centred around linearly variable bandpass filter 109 (such as Delta Optics Continuously Variable Filter). The bandpass filter 109 is placed at a focal point of the focusing lens 108. Bandpass filter 109 is preferably formed of a low pass filter 109a combined with a high pass filter 109b. Each filter 109a and 109b is formed of an optical element that has spectral properties that vary linearly along its length. The light beam traverses the low and high pass filters and exits the filters with a spectral shape or wavelength sub-interval that corresponds to a bandpass filter. The width and centre frequency of the spectral sub-interval is defined by the linear offset of the two filters. In another embodiment, the low and high pass filters are optically mounted in parallel, each with their own light source. The high and low pass filtered light is then recombined using a beam splitter before going through the focusing lens 108.

As shown in FIG. 3, the width of the passband of filter 109 is defined by the relative displacement of the two filters 109a and 109b in a lateral dimension perpendicular to the optical axis. Tunability of filter 109 across different centre wavelengths is performed by collective displacement of the two filters 109a and 109b together simultaneously in the lateral dimension. Control of filter 109 tuning is performed by controller 150 or a separate controller. Filter 109 may be mounted on translational mounts with a linear actuator such that the position of filter 109 is stepped incrementally. By way of example, filter 109 may be controlled to shift vertically downward to tune filter 109 across centre wavelengths. In this manner, collective movement of the filter elements in tandem translates directly to a change in the wavelength sub-interval of interest (centre wavelength tuning).

The tuning of filter 109 is performed such that, the stepping of filter positions of filter elements 109a and 109b to define wavelength sub-intervals occurs in temporal synchronicity with the integration time of image sensor 113. The filter may be configured to be tuned continuously or in steps. Where the filter position is controlled to move continuously, the wavelength sub-interval will vary slightly during the integration time of image sensor 113 (an image frame). This means that from the beginning of integration of image sensor 113 to the end, the centre wavelength of filter 109 moves slightly and therefore the overall wavelength sub-interval is a somewhat larger than an equivalent stationary interval.

As the initially non-collimated light source is difficult to precisely focus, the bandwidth is quite large (generally >20 nm). To minimise light loss, the linear displacement of the two filters 109a and 109b is controlled such that it approximates the diameter of the focused light source, as produced by focusing lens 108. In another embodiment, this part of system 100 could also be achieved by separating the filter and adding another location of focus or also by using one or more cylindrical lenses to focus only the light in a single axis and thus potentially lead to slightly narrower bandwidth for a given power.

Although described and illustrated using a transmissive system of lenses, it will be appreciated that some or all of the various lenses in apparatus 100 may be replaced with equivalent optical elements such as mirrors or prisms.

Dynamic Power Compensation

Most broadband light sources are not completely spectrally flat and the added effects of transmission, reflectivity and sensitivity of the different optical elements of the apparatus degrade the SNR for each recorded waveband. As LEDs have very rapid responses to power variation, the present system is configured to compensate for spectral flatness by adjusting LED power dynamically as required for each spectral waveband. The spectral non-flatness may be due to characteristics of the eye being imaged, such as retinal reflectivity, and/or due to characteristics of apparatus 100.

In these embodiments, controller 150 or another controller is fed a set of calibration data to compensate for this spectral non-flatness. In particular, controller 150 may store or access data corresponding to relative power levels in which to control light sources 103 and 104 at different wavelength sub-intervals. By way of example, controller 150 may store or access a lookup table such as the following:

TABLE 1

| Wavelength sub-interval | Compensation factor | LED drive current |
|---|---|---|
| 450 nm | 1.0 | 20 A |
| 500 nm | 0.6 | 12 A |
| 550 nm | 0.3 | 6 A |
| 600 nm | 0.3 | 6 A |
| 650 nm | 1.2 | 24 A |

Table 1 is illustrative only and, in practice, a larger number of wavelength sub-intervals would typically be used.

Using the exemplary data in Table 1, controller 150 is configured to reduce the drive current to one or both of the light sources to reduce their output power at times when filter 109 is transmitting the wavelength sub-intervals of 500 nm, 550 nm and 600 nm. Conversely, controller 150 is configured to increase the drive current to one or both of the light sources to increase their output power at times when filter 109 is transmitting the wavelength sub-interval 650 nm. This output power control is dynamic as it occurs dynamically while filter 109 is selectively scanning the centre wavelength across different wavelength sub-intervals of the desired spectral range.

Using the above dynamic power control, the power of the one or more light sources may be modulated dynamically as a function of filter wavelength to provide a respective predefined spectral power for each of the spectral sub-intervals. This can be used to compensate for spectral non-flatness arising from one or more of the illumination module and/or imaging module (e.g. optical absorption by the illumination and/or imaging modules). The power of the one or more light sources can also modulated to achieve a threshold SNR for the tissue being imaged.

The power of the one or more light sources may be modulated based on a sensitivity of the imaging sensor. The power of the one or more light sources can be modulated to obtain a target digital count value on the image sensor for a reference surface. The reference surface may be derived from a retinal reflectivity measured from a sample population of people (e.g. an average retinal reflectivity of 1,000 people).

In addition to compensating for spectral non-flatness, apparatus 100 may also compensate for spatial aberrations due to characteristics of apparatus 100 and eyes being imaged. This can be achieved through one or more calibration routines performed by controller 150 and described below.

Figure 4:
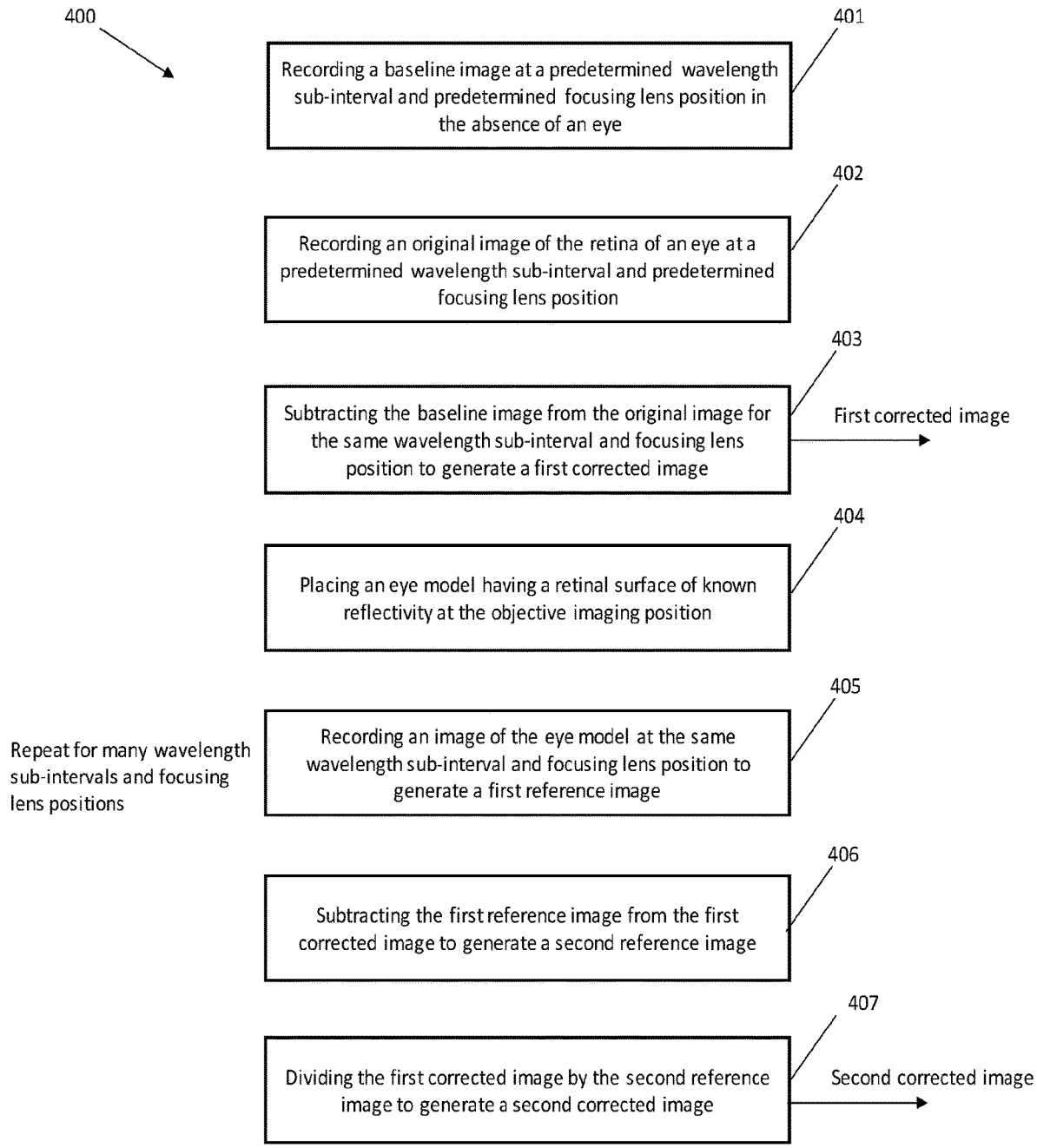
FIG. 4 is a flow chart illustrating the primary steps in a method to compensate for non-homogeneity of images recorded by a retinal imaging apparatus.

Referring now to FIG. 4, there is illustrated a method 400 of compensating for non-homogeneity of images recorded by a fundus imaging apparatus such as apparatus 100. At step 401, a baseline image is recorded at a predetermined wavelength sub-interval and at a predetermined focusing lens position to image internal reflections from components within apparatus 100. Here the optimal focus to compensate for eye refractive error is found in the IR and then the predefined movement of the focus position relative to this initial position is applied. The baseline image is an image taken by the apparatus in the absence of eye 102 and with external light blocked at an objective imaging position. This may be achieved by covering objective lens 122 or placing apparatus 100 in a dark room or dark cover/container or by placing an optical beam trap of dark absorbing surface at the focal plane of the annulus (where the eye 102 should be).

Step 401, may be repeated for any or all of the different wavelength sub-intervals and any or all of the different focusing lens positions available in apparatus 100. A baseline image is generated for each of the different wavelength sub-intervals and focusing lens positions. The baseline images may be stored in a database or memory accessible by controller 150 or stored in an external computer or on the cloud.

At step 402, an image of the fundus of eye 102 is captured by the apparatus at one of the same predetermined wavelength sub-intervals and at the same or similar predetermined focusing lens positions used in step 401 to generate an original image of the fundus.

At step 403, the baseline image corresponding to the same wavelength sub-interval and focusing lens position is subtracted from the original image to generate a first corrected image to compensate for internal reflections of the apparatus. The first corrected image may be stored in a database or memory accessible by controller 150 or stored in an external computer or on the cloud.

Steps 402 and 403 may be repeated for a plurality of wavelength sub-intervals and focusing lens positions corresponding to a normal hyperspectral scan of eye 102 by apparatus. The first corrected images may be stored and used to calibrate future original images taken by apparatus 100 across different wavelength sub-intervals and at different focusing lens positions. The first corrected images compensate at least partially for internal reflections off components within apparatus 100 that may affect some wavelengths more than others or be more prevalent at certain positions of focusing lens 108.

Method 400 may also optionally include further steps 404 to 407. Step 404 includes placing an eye model at the objective imaging position of apparatus 100. The eye model includes a retinal surface of known reflectivity. At step 405, an image of the eye model is recorded by apparatus 100 at one or many of the predetermined wavelength sub-intervals and at the predetermined focusing lens positions to generate corresponding reference images. These reference images may be referred to as white images as the retinal surface may be modelled as a white surface.

At step 406, the first corrected image is subtracted from the first reference image at a corresponding wavelength sub-interval and focusing lens position to generate a compensated image. Next, at step 507, the first corrected image is divided by the compensated image to obtain a second corrected image that at least partially compensates for intensity inhomogeneity of the apparatus.

Steps 405 to 407 may be performed for a plurality of wavelength sub-intervals and focusing lens positions at which original fundus images are captured.

This process is described in more detail below in relation to a spectral information recovery method.

In another embodiment of this apparatus, the integration time of the camera is adjusted dynamically to compensate for varying SNR ratios between the spectral wavebands.

In some embodiments, the spectral profile may be flattened or shaped using a customized filter in the light path. This may be used instead of or in conjunction with the dynamic spectral power control described above.

In some embodiments, using the dynamic power compensation methods described above, apparatus 100 is capable of imaging a fundus with a spatial flatness of field that is within 30% deviation.

Chromatic Aberration Correction

The focal length of a lens varies with the wavelength (which creates axial chromatic aberration). As a result, longer wavelengths focus at longer distances than shorter wavelengths for conventional lenses. One solution for axial chromatic aberration is to construct lenses composed of different types of glass, however this is costly and complex and may result in problematic back-reflections that degrade image quality. Embodiments of the present invention provide an alternative solution to compensate for chromatic aberration by adjusting the position of one or more of imaging lenses 114 and 118 for each waveband during image acquisition.

Referring again to FIG. 1, in one embodiment, comprised of an apparatus with a simple objective lens 122 (e.g. a single glass element), focussing lens 108 is moved linearly along the optical axis in synchrony with the relative lateral movement waveband selection using filter 109 to dynamically compensate for chromatic aberration. In another embodiment comprised of an apparatus with an achromatic objective lens 122 (e.g. with two glass elements), focusing lens 108 is moved quadratically in synchrony with the waveband selection using filter 109 to compensate for axial chromatic aberration. Chromatic aberration only requires subtle adjustment of the focusing lens 108 (compared to the movement required for refractive error compensation).

The movement for chromatic correction is made relative to the corrected refractive error position of a given eye.

Spectral Information Recovery Method

Apparatus 100 enables illumination of the fundus with a spectral profile having a wavelength sub-interval for each given position of the linearly variable bandpass filter 109. Each wavelength sub-interval may have a wider bandwidth than the steps between the intervals (and therefore partially overlap), which is not optimal for conventional hyperspectral imaging of the fundus. Described below is a method to effectively compensate for this spectral overlap and recover the information as if the illumination was with narrow and non-overlapping bandwidth.

The key requirements for this compensation are: (1) to be able to determine or measure the spectral profile of the filter 109 or of the illuminating light at each position of filter 109 used to image; and (2) that these measured spectral profiles for each position of filter 109 are linearly independent from each other. By design, apparatus 100 ensures that these requirements are met. Specifically, (1) full control of the illumination and synchronisation with the filter position enables accurate measurement of these parameters and (2) the translation from one position of filter 109 to the next will ensure independence of the measured spectral bands as no two spectral wavebands will be fully overlapping.

Although described in relation to apparatus 100 and filter 109, it will be appreciated that this spectral information recovery method may be performed with other systems and with different tuneable filters.

Figure 5:
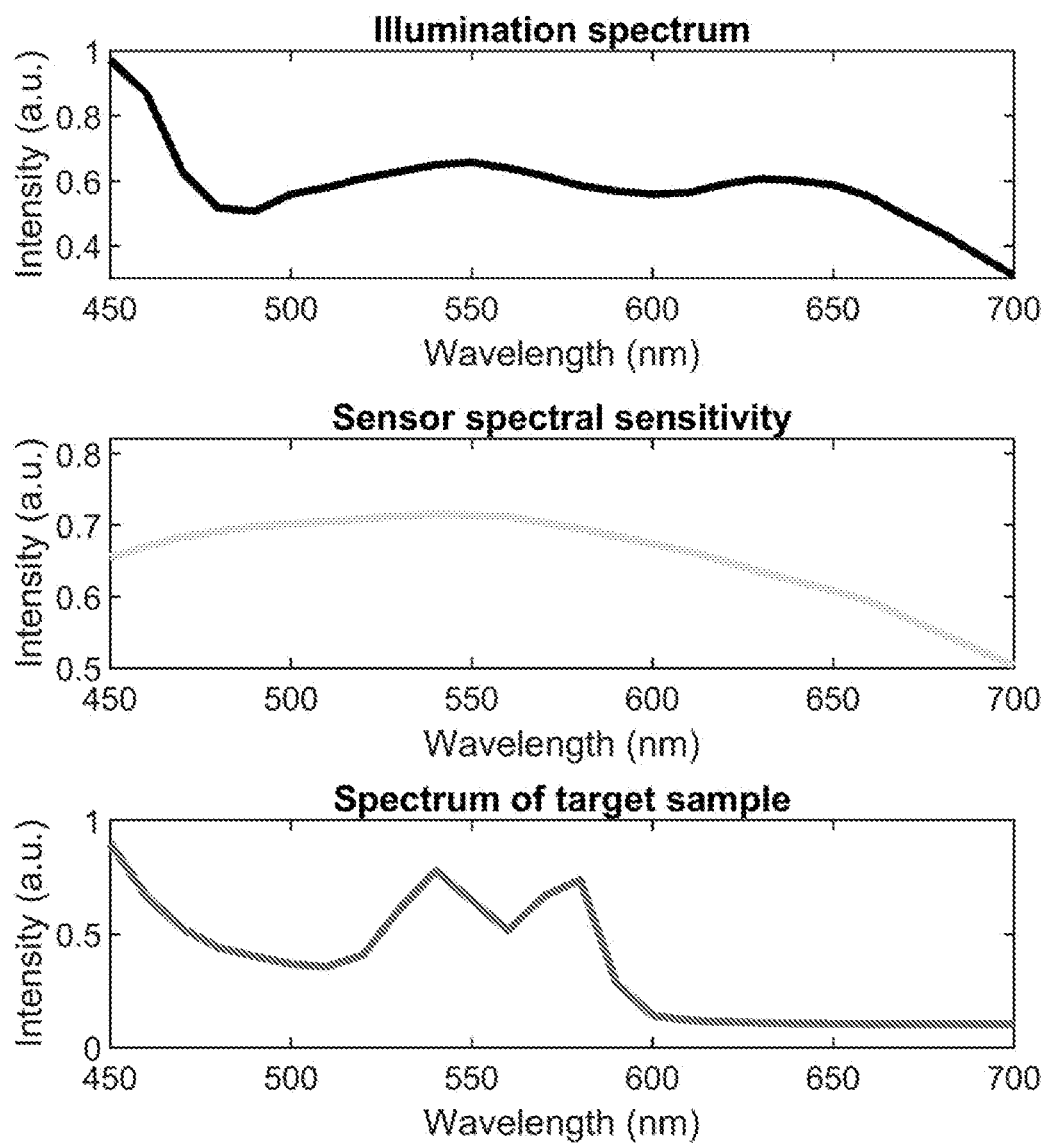
FIG. 5 shows graphs of an illumination spectrum, sensor spectral sensitivity and a spectrum of a target sample as a function of wavelength across a spectral range of 450 nm to 700 nm.

FIG. 5 illustrates data relevant to the spectral recovery method. The top panel illustrates an illumination spectrum that may correspond to the spectrum of LED 103 or 104 used to illuminate the eye 102. The middle panel illustrates a sensor spectral sensitivity that may represent the wavelength sensitivity or spectral response of image sensor 113. The bottom panel represents the ideal fundus (or retinal) reflectivity spectrum that is to be extracted.

Figure 6A:
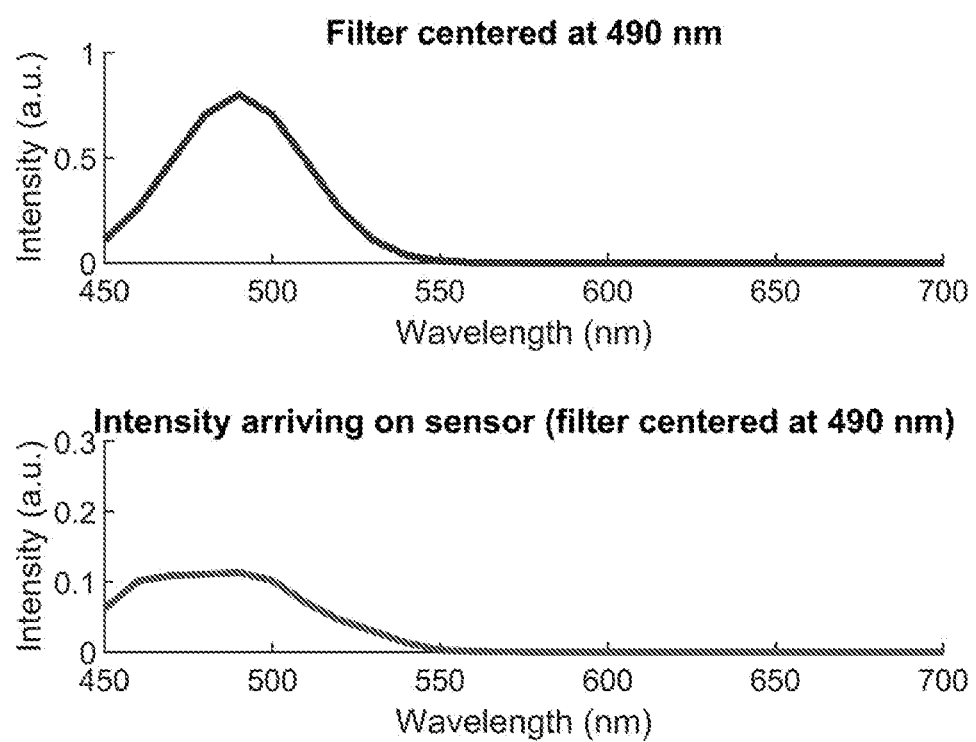
FIG. 6A shows graphs of a filter response of a spectral filter having a passband centred at 490 nm and a corresponding detected image sensor intensity.
Figure 6B:
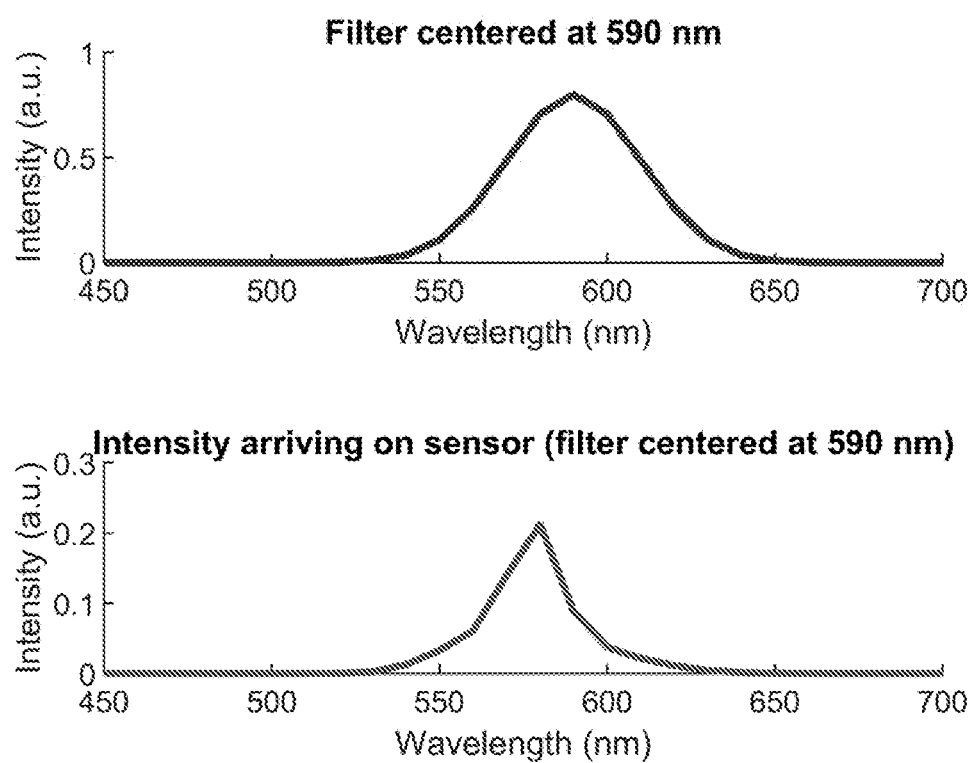
FIG. 6B shows graphs of a filter response of a spectral filter having a passband centred at 590 nm and a corresponding detected image sensor intensity.
Figure 6C:
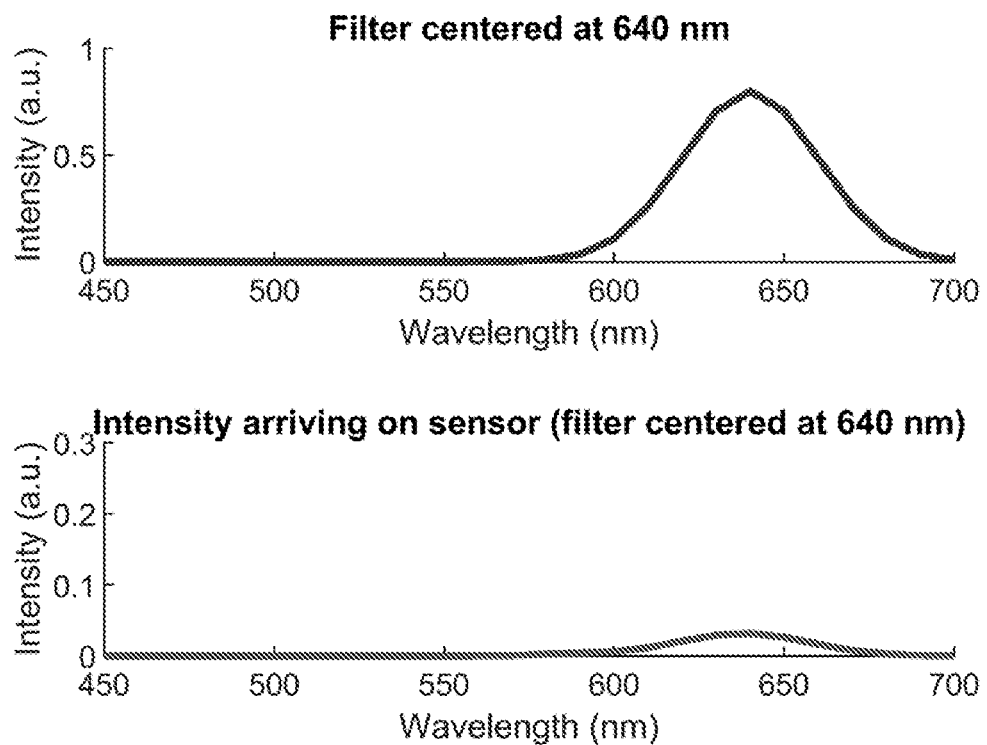
FIG. 6C shows graphs of a filter response of a spectral filter having a passband centred at 640 nm and a corresponding detected image sensor intensity.

FIG. 6A illustrates a filter response or spectral transmission when the filter (e.g. filter 109) passband is centred at 490 nm. FIG. 6A also illustrates the corresponding intensity spectrum arriving at the image sensor for that filter position and integrated according to the sensor spectral sensitivity to yield a single digital count. FIGS. 6B and 6C illustrate the corresponding data for when the filter passband is centred at 590 nm and 640 nm respectively.

Figure 7:
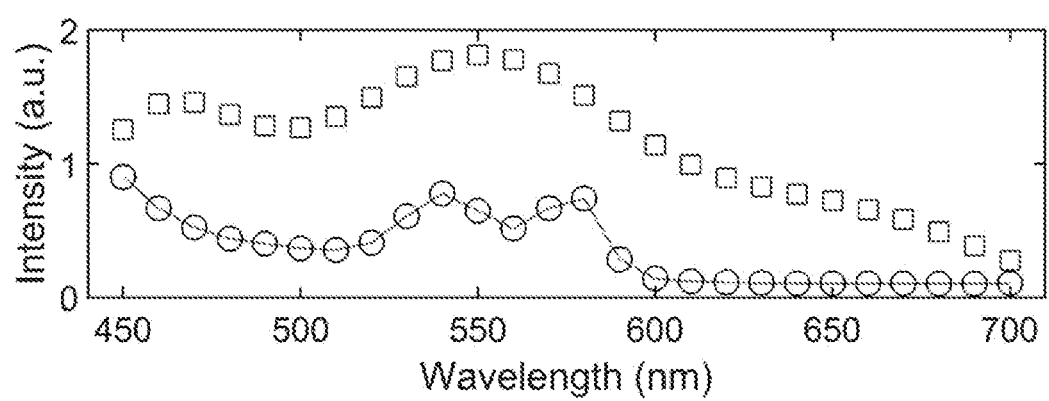
FIG. 7 is a graph of intensity versus wavelength illustrating an actual intensity curve of a desired spectral property (straight line), an image sensor readout for measurements captured at a plurality of positions across a desired spectral band (squares) and a resulting recovered spectral readout after a spectral recovery method has been applied (circles)

Moving the tuneable filter for all the required positions k gives a spectral readout illustrated by the squares in FIG. 7. However, due to overlap of the spectral bands, the information recovered at this stage does not correspond directly to the actual spectral property of the fundus, which is illustrated by the lower line curve of FIG. 7. By applying a spectral information recovery method described below, the target spectral property of the fundus such as reflectance can be accurately recovered, which is illustrated by the black circles in FIG. 7. As can be seen, the target spectral property closely matches the real spectral property of the fundus.

The digital count on the sensor for each acquisition with the tuneable filter can be written as follows:

$$dc[k] = \int_{\lambda min}^{\lambda max} f[k](\lambda) \cdot s(\lambda) \cdot l(\lambda) \cdot t_{ill}(\lambda) \cdot t_{im}(\lambda) \cdot r(\lambda) d(\lambda)$$

where dc is the digital count, $k \in [1, K]$ is the filter position number, $f(\lambda)$ is the filter spectral transmission at position k, $s(\lambda)$ is the sensor sensitivity, $l(\lambda)$ is the light source spectral profile, $t_{ill}(\lambda)$ is the spectral transmission of the illumination system, $t_{im}(\lambda)$ is the spectral transmission of the imaging system and $r(\lambda)$ is the fundus reflectance representing the useful information to be sampled over K wavebands. Other terms such as transmission of and reflectivity of other optical components can also be taken into account without loss of generality.

This continuous scale integration can be approximated to any desired level of accuracy of the sensor value as a sum over P discrete wavelengths such that:

$$dc[k] = \sum_{\lambda=1}^{P} f[k](\lambda) \cdot s(\lambda) \cdot l(\lambda) \cdot t_{ill}(\lambda) \cdot t_{im}(\lambda) \cdot r(\lambda)$$

At this point, it is assumed that P is at least as large as K, the number of independent wavebands to recover. This summation can be rewritten as a matrix equation such that:

$DC = F \cdot \text{diag}(s) \cdot \text{diag}(l) \cdot \text{diag}(t_{ill}) \cdot \text{diag}(t_{im}) \cdot r$ where DC is a K dimensional vector containing the digital count measured on the sensor for each filter position, F is the K×P matrix containing the spectral transmission at each filter position, $s, l, t_{ill}, t_{im}$ are the P dimensional vectors representation of the sensor sensitivity, light source spectral profile, illumination system spectral transmission and imaging system spectral transmission respectively. The operator diag(·) places the vector elements in the corresponding diagonal matrix of dimension P×P. The vector r is the P dimensional reflectance vector desired to approximate in dimension K such that:

$\hat{r} = D \cdot r$ where D is a user-defined downsampling matrix of dimension K×P. For example, if the first row of the downsampling matrix was d1=[⅓, ⅓, ⅓, 0, . . . , 0], it would take a uniformly weighted average of the three first element of r and place them in the first element of r̂. Uniform or Gaussian distribution are examples of such down sampling matrices.

Since only access to the K-dimensional vector DC is available, it is necessary to find a calibration matrix C of dimension K×K such that:

$\hat{r} = C \cdot DC$

Replacing DC by the equation above gives:

$\hat{r} = C \cdot F \cdot \text{diag}(s) \cdot \text{diag}(l) \cdot \text{diag}(t_{ill}) \cdot \text{diag}(t_{im}) \cdot r$ Substituting $\hat{r} = D \cdot r$ leads to:

$D \cdot r = C \cdot F \cdot \text{diag}(s) \cdot \text{diag}(l) \cdot \text{diag}(t_{ill}) \cdot \text{diag}(t_{im}) \cdot r$ Which reduces to $D = C \cdot F \cdot \text{diag}(s) \cdot \text{diag}(l) \cdot \text{diag}(t_{ill}) \cdot \text{diag}(t_{im})$ Assuming that the elements of the diagonal matrices are non-zeros, then:

$D \cdot \text{diag}(t_{im})^{-1} \cdot \text{diag}(t_{ill})^{-1} \cdot \text{diag}(l)^{-1} \cdot \text{diag}(s)^{-1} = C \cdot F$ Multiplying on the right by the transpose of the matrix F gives:

$$D \cdot \text{diag}(t_{im})^{-1} \cdot \text{diag}(t_{ill})^{-1} \cdot \text{diag}(l)^{-1} \cdot \text{diag}(s)^{-1} \cdot F^T = C \cdot F \cdot F^T$$

As previously explained, it is assumed that the matrix F contains K linearly independent rows and therefore the matrix $F \cdot F^T$ is invertible. Right multiplying by $(F \cdot F^T)^{-1}$ gives the following formula for the calibration matrix C:

$$C = D \cdot \text{diag}(t_{im})^{-1} \cdot \text{diag}(t_{ill})^{-1} \cdot \text{diag}(l)^{-1} \cdot \text{diag}(s)^{-1} \cdot F^T \cdot (F \cdot F^T)^{-1}$$

Altogether, from the measured digital count DC, the reflectance values can be estimated by using the following formula:

$$\hat{r} = C \cdot DC = D \cdot \text{diag}(t_{im})^{-1} \cdot \text{diag}(t_{ill})^{-1} \cdot \text{diag}(l)^{-1} \cdot \text{diag}(s)^{-1} \cdot F^T \cdot (F \cdot F^T)^{-1} \cdot DC$$

It is possible that some of the diagonal matrices cannot be measured or estimated. In this context, ignoring one or more of the diagonal matrices would lead to a biased estimate of $\hat{r}$. Assuming that a surface of known reflectivity can be imaged in the same condition as the retina, the unbiased estimate of $\hat{r}$ can be recovered as follows:

$$\hat{r}[k] = \frac{\hat{r}_{biased}[k]}{\hat{r}_{biased}^{white}[k]} \cdot r^{known}[k],$$

for $$k \in [1, K]$$

The term $r^{known}$ can be derived from its tabulated value by first resampling the wavelength to the one used for the filter matrix F and then multiplying by the down sampling matrix F. In the case of a white reference, $r^{known}$ for all values and can be omitted, which lead to the simplified equation:

$$\hat{r}[k] = \frac{\hat{r}_{biased}[k]}{\hat{r}_{biased}^{white}[k]},$$

for $$k \in [1, K]$$

$\hat{r}[k]$ represents the estimated retinal fundus reflectance that can be recovered from the series of partially spectrally overlapping images obtained by apparatus 100.

The spectral information recovery method involves the following steps:
a) Determine the filter transmission spectra for K positions of filter 109. This may include obtaining actual measurements of the illumination spectra or determining approximations thereof.
b) Optionally determine or measure the other spectral properties of the system such as sensor sensitivity, light source spectrum, optics transmission
c) Optionally resample the spectra from step a) or b) above over P more convenient wavelengths.
d) Populate the down-sampling matrix D;
e) Calculate a calibration matrix C (with dimension K×K) with the filter transmission spectra for the K spectral sub-intervals and optionally with the other measured or derive spectra. As mentioned above, this filter transmission matrix should be well conditioned for most practical applications and its right pseudo inverse exists. The other P-dimensional matrices are diagonal and can also be inverted assuming no entry on the diagonal is zero. For the purpose of the claims, the right pseudo-inverse operation or other type of matrix inversions will be referred to as an inverse operation. The calibration matrix may also include information regarding the light source spectrum, image sensor wavelength sensitivity and spectral transmission of the illumination and imaging system.
f) Record a hyperspectral image in the same acquisition condition as the calibration matrix. The hyperspectral image including a plurality (K) of images of light returned from an eye of a subject, wherein at least one image is captured at each of K positions of filter 109. Each filter position corresponds to a wavelength sub-interval that has a finite bandwidth and which may be partially overlapping with one or more adjacent sub-intervals. That is, the bandwidth of a spectral sub-interval may be wider than the spacing of the centre wavelengths of adjacent sub-intervals.
g) Register the K images so that corresponding pixels of the images are aligned to a same spatial region of the eye.
h) Transforming the digital counts DC (of dimension K) for each pixel (i,j) of the hyperspectral image into reflectance values $r_1$ (of dimension K) by multiplying the DC vectors by the calibration matrix C as follows:

$$r1(i,j) = C \times DC(i,j)$$

To compensate for illumination homogeneity and remove internal reflection of the camera, a white target (W) and baseline target (BL) can be imaged using the same acquisition setting (filter position and focusing lens position). In this case to recover the reflectance data $R_2$, the equation reads as follows:

$$r_W(i,j) = C \times DC_W(i,j)$$

$$rr_{BL}(i,j) = C \times DC_{BL}(i,j)$$

$$r_2(i,j) = (r_1(i,j) - r_{BL}(i,j))/(r_w(i,j) - r_{BL}(i,j))$$

The image acquisition and spectral information recovery process can be summarised as follows:
1) Measure with a spectroradiometer the transmission spectrum for each position of the filter (or otherwise estimate this illumination spectrum);
2) [optional] resample the measured spectra to the desired wavebands;
3) [optional] measure with a spectroradiometer (or estimate) the source spectrum, image sensor wavelength sensitivity and spectral transmission of the illumination and imaging system;
4) Populate the down sampling matrix D;
5) Calculate the calibration matrix D;
6) [optional] Record a digital count (DC) image of an artificial eye with known reflectivity (usually white) in place of the retina over each spectral interval;
7) [optional] Record a DC image of a very absorbing black surface positioned at the pupil plane to record light that get back reflected form within the system over each spectral interval;
8) [optional] record a dark current image;
9) Record a DC image of an eye over each spectral interval;
10) Multiply each spectral pixel of each DC image by the calibration matrix C to obtain the corresponding reflectance hyperspectral image; and 10) [optional] correct the reflectance eye image using the white image, baseline image and dark image;

The steps for hyperspectral image acquisition of an eye of a subject can be summarised as follows:
1) Subject positioned in front of the apparatus;
2) Fixation target switched ON;
3) Main light source activated with filter on infrared (IR) position (quasi invisible for patient);
4) Alignment of camera to provide correct visualisation of the patient's fundus;
5) Focus tuning to improve image resolution;
6) Fixation target switched OFF;
7) Start acquisition sequence (modulated power, movement of spectral filter, movement of focus, camera frame recording;
8) Acquisition finalised and image saved; and
9) [Optional] Acquire another image at a different location of the fundus (movement of the fixation target) of the same eye or acquire image of the fellow eye).

Other Embodiments

Referring now to FIGS. 8 to 11, there are illustrated alternative embodiments of apparatus 100.

Figure 8:
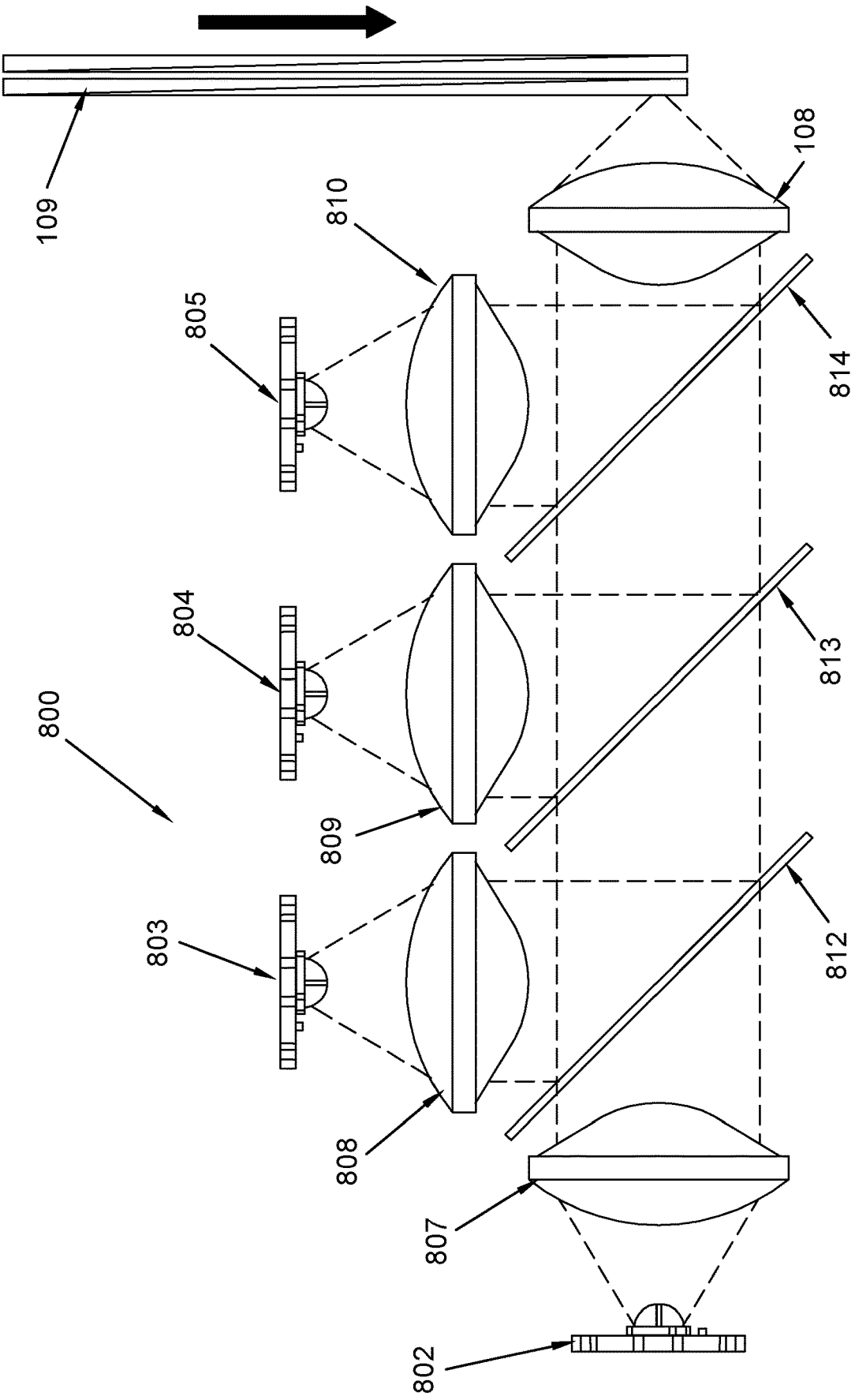
FIG. 8 is a schematic illustration of a section of an illumination module of a retinal imaging apparatus according to a second embodiment.

FIG. 8 illustrates a section of the illumination module of an apparatus 800 including four LEDs 802-805 representing light sources for illuminating an eye. Apparatus 800 functions in a similar manner to that of apparatus 100 described above. However, the inclusion of four light sources allows for greater spectral and power control across the desired spectral range. By way of example, LEDs 802-805 may have different power at different peak wavelengths and/or may be controlled to be driven at different power levels. One LED may be used to illuminate the eye in the infrared range for system alignment and the remaining three LEDs may be used to illuminate in the visible range for standard image capture.

In apparatus 800, LED 802 is disposed perpendicular to LEDs 803-805 with each LED having a corresponding collimating lens 807-810. To combine the beams from each of the LEDs 802-805, three beam splitters 812-814 are disposed in the optical path. Beam splitters 807-809 combine the beams so that they collectively pass through focussing lens 108 to the remainder of the optical system. By way of example, beam splitters 807-809 may be 50:50 beam splitters.

Figure 9:
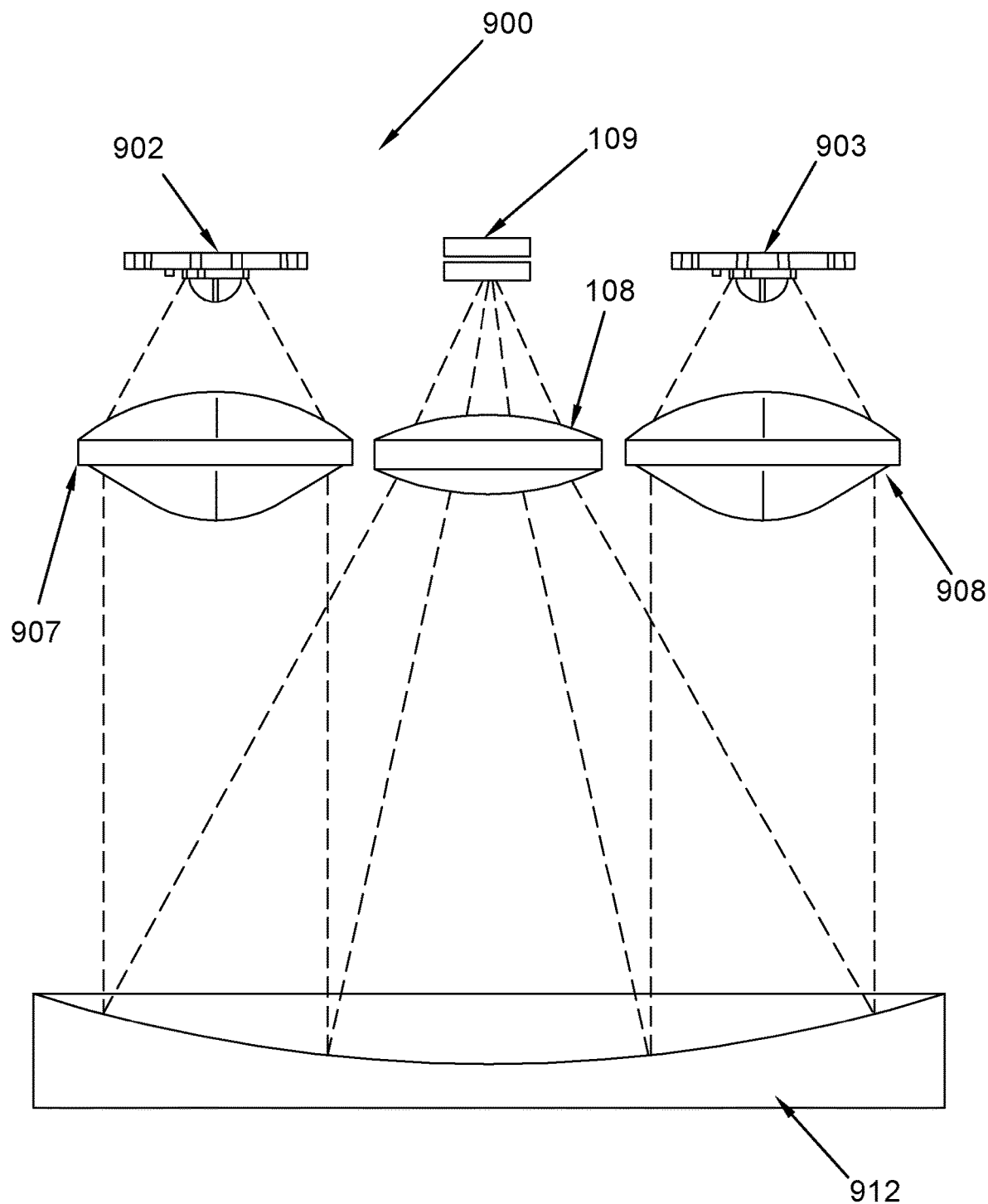
FIG. 9 is a schematic plan view of a section of an illumination module of a retinal imaging apparatus according to a third embodiment.
Figure 10:
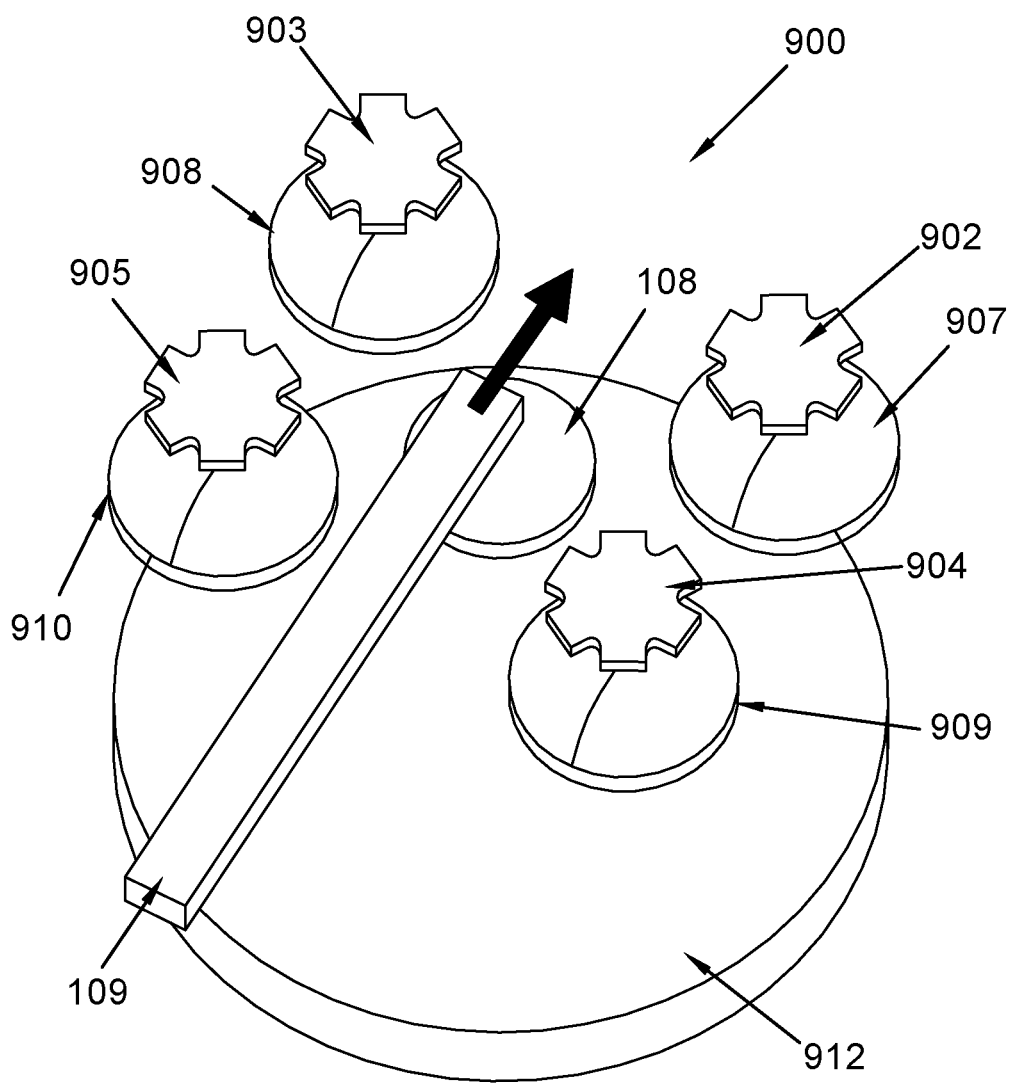
FIG. 10 is a schematic perspective view of the third embodiment retinal imaging apparatus of FIG. 9.

FIGS. 9 and 10 illustrate a section of the illumination module of an apparatus 900 including an array of four LEDs 902-905 representing light sources for illuminating an eye. LEDs 902-905 are positioned to direct light through corresponding lenses 907-910 and onto a parabolic mirror 912. Parabolic mirror 912 in turn combines the light from each LED 902-905 and directs the combined light to focussing lens 108 and onto filter 109. Apparatus 900 has the advantage of avoiding beam splitters at the input path, which can increase the overall optical power that passes through the optical system.

Figure 11:
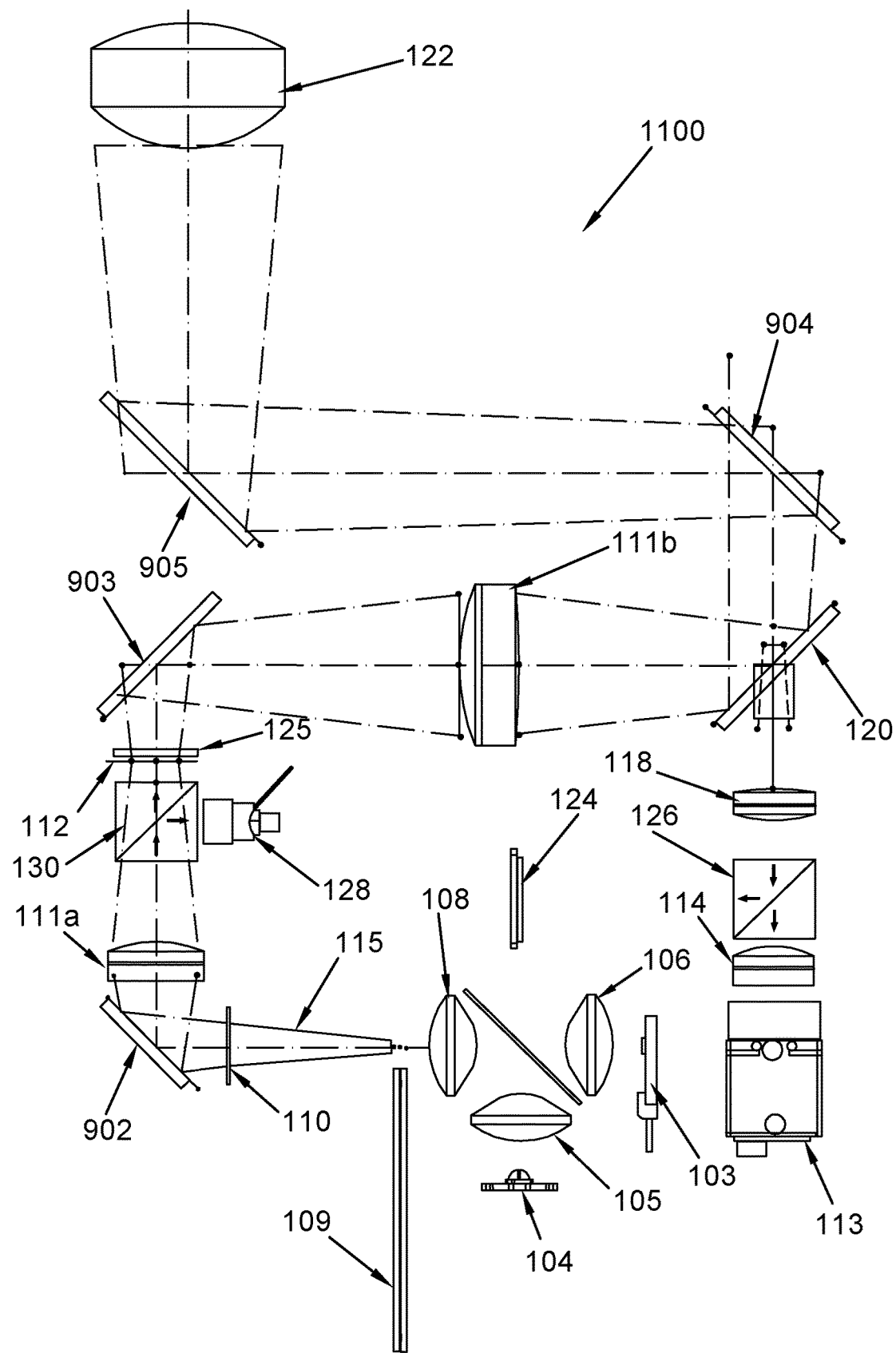
FIG. 11 is a schematic illustration of a retinal imaging apparatus according to a fourth embodiment.

FIG. 11 illustrates an alternative apparatus 1100 having a different optical path to that of apparatus 100 described above. Folding mirrors 902-905 are used to fold the optical beam around the optical path to objective lens 122 and the eye (not shown). Example central and peripheral light rays are shown in FIG. 11 as dash-dot lines.

Interpretation

Reference to spectral widths in this specification such as "bandwidth", "wavelength sub-interval" and "passband" are intended to refer to a standard measure such as the full width at half maximum (FWHM) measurement. The FWHM measurement defines a spectral width as the width of a spectral peak at which the amplitude is equal to half of its maximum value.

Throughout this specification use of the term "fundus" is intended to refer to a portion of the eye that comprises at least the retina and optionally other parts such as the optic disc, retinal blood vessels, retinal pigment epithelium and choroid. It is intended that a fundus image includes at least a retinal image plus optionally information about these other ocular regions.

Unless specifically stated otherwise, as apparent from the following discussions, it is appreciated that throughout the specification discussions utilizing terms such as "processing," "computing," "calculating," "determining", analyzing" or the like, refer to the action and/or processes of a computer or computing system, or similar electronic computing device, that manipulate and/or transform data represented as physical, such as electronic, quantities into other data similarly represented as physical quantities.

In a similar manner, the term "controller" or "processor" may refer to any device or portion of a device that processes electronic data, e.g., from registers and/or memory to transform that electronic data into other electronic data that, e.g., may be stored in registers and/or memory. A "computer" or a "computing machine" or a "computing platform" may include one or more processors.

Reference throughout this specification to "one embodiment", "some embodiments" or "an embodiment" means that a particular feature, structure or characteristic described in connection with the embodiment is included in at least one embodiment of the present disclosure. Thus, appearances of the phrases "in one embodiment", "in some embodiments" or "in an embodiment" in various places throughout this specification are not necessarily all referring to the same embodiment. Furthermore, the particular features, structures or characteristics may be combined in any suitable manner, as would be apparent to one of ordinary skill in the art from this disclosure, in one or more embodiments.

As used herein, unless otherwise specified the use of the ordinal adjectives "first", "second", "third", etc., to describe a common object, merely indicate that different instances of like objects are being referred to, and are not intended to imply that the objects so described must be in a given sequence, either temporally, spatially, in ranking, or in any other manner.

In the claims below and the description herein, any one of the terms comprising, comprised of or which comprises is an open term that means including at least the elements/features that follow, but not excluding others. Thus, the term comprising, when used in the claims, should not be interpreted as being limitative to the means or elements or steps listed thereafter. For example, the scope of the expression a device comprising A and B should not be limited to devices consisting only of elements A and B. Any one of the terms including or which includes or that includes as used herein is also an open term that also means including at least the elements/features that follow the term, but not excluding others. Thus, including is synonymous with and means comprising.

It should be appreciated that in the above description of exemplary embodiments of the disclosure, various features of the disclosure are sometimes grouped together in a single embodiment, FIG., or description thereof for the purpose of streamlining the disclosure and aiding in the understanding of one or more of the various inventive aspects. This method of disclosure, however, is not to be interpreted as reflecting an intention that the claims require more features than are expressly recited in each claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment of this disclosure.

Furthermore, while some embodiments described herein include some but not other features included in other embodiments, combinations of features of different embodiments are meant to be within the scope of the disclosure, and form different embodiments, as would be understood by those skilled in the art. For example, in the following claims, any of the claimed embodiments can be used in any combination.

In the description provided herein, numerous specific details are set forth. However, it is understood that embodiments of the disclosure may be practiced without these specific details. In other instances, well-known methods, structures and techniques have not been shown in detail in order not to obscure an understanding of this description.

Similarly, it is to be noticed that the term coupled, when used in the claims, should not be interpreted as being limited to direct connections only. The terms "coupled" and "connected," along with their derivatives, may be used. It should be understood that these terms are not intended as synonyms for each other. Thus, the scope of the expression a device A coupled to a device B should not be limited to devices or systems wherein an output of device A is directly connected to an input of device B. It means that there exists a path between an output of A and an input of B which may be a path including other devices or means. "Coupled" may mean that two or more elements are either in direct physical, electrical or optical contact, or that two or more elements are not in direct contact with each other but yet still co-operate or interact with each other.

Embodiments described herein are intended to cover any adaptations or variations of the present invention. Although the present invention has been described and explained in terms of particular exemplary embodiments, one skilled in the art will realize that additional embodiments can be readily envisioned that are within the scope of the present invention.

The claims defining the invention are as follows:

1. A non-mydriatic ocular fundus imaging apparatus including:
    an illumination module having:
        one or more light sources configured to generate light at wavelengths within a desired spectral range;
        a first optical assembly to shape and direct the light onto an eye of a subject; and
        a tuneable bandpass filter to select a wavelength sub-interval within the desired spectral range;
    an imaging module having:
        a second optical assembly to collect light returned from the eye of the subject and to project the returned light from the eye onto an image sensor, the second optical assembly including one or more optical elements capable of compensating for ocular variation; and
        an image sensor configured to image the returned light to generate a non-mydriatic image of the ocular fundus at the wavelength sub-interval; and
    one or more controllers configured to:
        tune the tuneable bandpass filter between a plurality of wavelength sub-intervals within the desired spectral range;
        control the image sensor to generate a plurality of non-mydriatic images of the ocular fundus at each of the plurality of wavelength sub-intervals; and
        dynamically control the power of the one or more light sources to provide a respective predefined power level for each of the plurality of wavelength sub-intervals;
    wherein the tuneable bandpass filter and the image sensor are synchronized by the one or more controllers so as to capture images at different wavelength sub-intervals within the desired spectral range; and
    wherein the plurality of non-mydriatic images of the ocular fundus is captured within a time of 300 milliseconds.

2. The apparatus of claim 1 wherein the tuneable bandpass filter is tuneable between the infrared wavelength range and the blue wavelength range.

3. The apparatus of claim 2 wherein the tuneable bandpass filter is configured to be tuned from the infrared wavelength range to the blue wavelength range such that the image sensor captures one or more first images in the infrared wavelength range and subsequently captures one or more second images in the visible wavelength range.

4. The apparatus of claim 2 wherein the tuneable bandpass filter is configured to be tuned with predefined steps at a predefined speed.

5. The apparatus of claim 1 wherein the respective predefined power levels for each of the spectral sub-intervals are selected to compensate for spectral non-flatness arising from one or more of the illumination module and/or imaging module.

6. The apparatus of claim 1 wherein the power of the one or more light sources is controlled to achieve a threshold signal-to-noise ratio for the tissue being imaged.

7. The apparatus of claim 1 wherein the power of the one or more light sources is controlled to obtain a target digital count value on the image sensor for a reference surface.

8. The apparatus of claim 7 wherein the reference surface is derived from a retinal reflectivity of a sample population.

9. The apparatus of claim 1 wherein the power of the one or more light sources is controlled to compensate for an optical absorption by the illumination and/or imaging modules.

10. The apparatus of claim 1 wherein the power of the one or more light sources is controlled based on a sensitivity of the imaging sensor.

11. The apparatus of claim 1 wherein the second optical assembly includes a focusing lens sub-system having one or more focusing lenses moveable in position along an optical axis, and wherein the axial movement of the one or more focusing lenses is synchronized with a wavelength filter movement of the tuneable bandpass filter to give an improved focusing at the image sensor for each of a plurality of spectral sub-intervals to compensate for chromatic aberrations.

12. The apparatus of claim 1 wherein the focusing lens movement is nonlinear with respect to the wavelength tuning of the tuneable bandpass filter.

13. The apparatus of claim 1 wherein the focusing lens movement is quadratic with respect to the wavelength tuning of the tuneable bandpass filters.

14. The apparatus of claim 1 wherein the tuneable bandpass filter has a spectral bandwidth that is larger than the steps between the wavelength sub-intervals.

15. The apparatus of claim 1 wherein the tuneable bandpass filter is a linearly variable bandpass filter.

16. The apparatus of claim 1 wherein the illumination module includes an annulus disposed after the tuneable bandpass filter for shaping the light at a pupil plane of the eye of the subject.

17. The apparatus of claim 16 including an optical diffuser disposed between the tuneable bandpass filter and annulus.

18. The apparatus of claim 17 including a homogenizing rod disposed between the tuneable bandpass filter and annulus.

19. The apparatus of claim 18 wherein the optical diffuser is integral with or attached to the homogenizing rod.

20. The apparatus of claim 1 wherein the one or more light sources have a spectral bandwidth covering at least the range from 450 nm to 720 nm and include a first LED having output power in the infrared wavelength range and a second LED having output power in the visible range.

* * * * *